US012725709B2

(12) United States Patent
Sun et al.

(10) Patent No.: US 12,725,709 B2
(45) Date of Patent: Sep. 1, 2026

(54) SYSTEMS AND METHODS FOR RECONSTRUCTING A 3D MEDICAL REPRESENTATION BASED ON SCREEN CAPTURES

(71) Applicant: Shanghai United Imaging Intelligence Co., Ltd., Shanghai (CN)

(72) Inventors: Shanhui Sun, Lexington, MA (US); Xiao Chen, Lexington, MA (US); Terrence Chen, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 0 days.

(21) Appl. No.: 18/986,331

(22) Filed: Dec. 18, 2024

(65) Prior Publication Data

US 2026/0171243 A1 Jun. 18, 2026

(51) Int. Cl.

| | |
|---|---|
| ***G16H 50/20*** | (2018.01) |
| ***G16H 15/00*** | (2018.01) |
| ***G16H 30/40*** | (2018.01) |

(52) U.S. Cl.

CPC ............. *G16H 50/20* (2018.01); *G16H 15/00* (2018.01); *G16H 30/40* (2018.01)

(58) Field of Classification Search

CPC ............................... G16H 15/00; G16H 30/40

See application file for complete search history.

(56) References Cited

U.S. PATENT DOCUMENTS 6,463,438 B1 * 10/2002 Veltri .................. G06V 20/695 706/15
7,567,707 B2 * 7/2009 Willamowski ....... G06V 40/193 358/518
7,738,683 B2 * 6/2010 Cahill .................. G06T 7/0012 382/128
7,764,846 B2 * 7/2010 Marchesotti ......... G06V 40/193 382/254
7,860,283 B2 * 12/2010 Begelman ................ G06T 7/11 600/407
8,634,614 B2 * 1/2014 Madsen .................... G06T 7/41 382/128
9,119,540 B2 * 9/2015 Sharma ................ G06T 7/0016

(Continued)

OTHER PUBLICATIONS

Truong, Jun. 2024, ArXiv, pp. 1-9.*
Yang, 2021 pp. 2228-2235.*
Zhou, Sensors, Apr. 2024, pp. 1-36.*

*Primary Examiner* — Michael I Ezewoko
(74) *Attorney, Agent, or Firm* — Zhong Law, LLC

(57) ABSTRACT

Disclosed herein are systems, methods, and instrumentalities associated with reconstructing a 3D representation of an anatomical structure based on a screen recording of a display while medical images of the anatomical structure are shown on the display. A plurality of medical images of the anatomical structure may be extracted from the screen recording, and one or more parameters for reconstructing the 3D representation of the anatomical structure based on the extracted medical images may be determined. The 3D representation of the anatomical structure may then be reconstructed based on the extracted medical images and the one or more determined parameters. From the 3D representation of the anatomical structure, abnormalities may be detected, and medical reporting may be performed using pre-trained machine-learning models.

13 Claims, 6 Drawing Sheets

(56) References Cited

U.S. PATENT DOCUMENTS 9,173,626 B2 * 11/2015 Kiraly .................... A61B 6/12
9,406,142 B2 * 8/2016 Gorman, III ........... G06T 7/174
9,495,752 B2 * 11/2016 Wu ........................ G06T 7/143
9,519,981 B2 * 12/2016 Sudarsky ............... G06T 11/26
9,569,736 B1 * 2/2017 Ghesu ................. A61B 5/7264
9,617,511 B2 * 4/2017 Chen ................... C12N 5/0657
9,700,219 B2 * 7/2017 Sharma ............... G06V 10/774
9,707,400 B2 * 7/2017 Grenz ................... A61B 6/466
9,770,533 B2 * 9/2017 Ling .................. A61L 27/3821
9,792,531 B2 * 10/2017 Georgescu .......... A61B 5/0044
9,898,858 B2 * 2/2018 Tamersoy ............ G06T 17/205
9,934,566 B2 * 4/2018 Sun ...................... A61B 6/032
9,947,102 B2 * 4/2018 Xu ..................... G06F 18/2411
9,965,863 B2 * 5/2018 Xu ........................ G06N 3/045
9,968,257 B1 * 5/2018 Burt .................... A61B 5/0035
9,996,664 B2 * 6/2018 Lloyd .................... G06F 16/33
10,043,088 B2 * 8/2018 Odry ............... G06V 30/19173
10,073,848 B2 * 9/2018 Kluckner ............. G06F 16/434
10,134,141 B2 * 11/2018 Xu ........................ G06N 3/045
10,143,384 B2 * 12/2018 Chen ................... A61B 5/0044
10,186,038 B1 * 1/2019 Kluckner ................. G06T 7/70
10,192,129 B2 * 1/2019 Price ..................... G06N 3/045
10,302,714 B2 * 5/2019 Chen ..................... G01R 33/34
10,304,569 B2 * 5/2019 Grady ................... G06T 7/0016
10,335,115 B2 * 7/2019 Grbic ....................... G06T 7/33
10,346,986 B2 * 7/2019 Xu ........................ G06N 3/045
10,373,313 B2 * 8/2019 Ghesu .................. G06T 7/0012
10,387,765 B2 * 8/2019 Mailhe .................... G06N 3/02
10,426,442 B1 * 10/2019 Schnorr ................. A61B 8/085
10,430,551 B2 * 10/2019 Wang .................... G16H 30/20
10,507,002 B2 * 12/2019 Singh ...................... A61B 6/40
10,521,927 B2 * 12/2019 Teixeira .................. A61B 6/08
10,698,063 B2 * 6/2020 Braun ............. G01R 33/56509
10,699,163 B1 * 6/2020 Shah .................... G06F 18/214
10,733,788 B2 * 8/2020 Ceccaldi ............... G06N 3/006
10,849,561 B2 * 12/2020 Huang ................. A61B 5/7207
10,852,379 B2 * 12/2020 Chen ................. G01R 33/4818
10,854,339 B2 * 12/2020 Grady ................. A61B 5/7271
10,866,298 B2 * 12/2020 Arberet ............. G01R 33/5602
10,867,384 B2 * 12/2020 Song ................... A61B 5/0037
10,871,535 B2 * 12/2020 Braun ................... G01R 33/50
10,871,536 B2 * 12/2020 Golden ............. G01R 33/5608
10,878,219 B2 * 12/2020 Zhou .................... G06F 18/285
10,902,651 B2 * 1/2021 Huang .............. G01R 33/4818
10,922,816 B2 * 2/2021 Huang .................. G16H 10/60
10,950,026 B2 * 3/2021 Wu ...................... G06N 3/0495
10,957,041 B2 * 3/2021 Yip .......................... G06T 1/20
10,991,092 B2 * 4/2021 Braun .................. G01R 33/543
11,062,488 B2 * 7/2021 Arberet ............. G01R 33/4828
11,100,647 B2 * 8/2021 Nikolov .............. A61B 5/7267
11,107,270 B2 * 8/2021 Kirchberg ........... G01B 11/026
11,127,158 B2 * 9/2021 Karanam ............ G06N 3/0464
11,172,889 B2 * 11/2021 Park ...................... A61B 5/055
11,200,668 B2 * 12/2021 Chun .................... G06V 10/82
11,227,389 B2 * 1/2022 Song ....................... G06N 3/02
11,232,554 B1 * 1/2022 Do ..................... G06F 18/2113
11,255,943 B2 * 2/2022 Liu ...................... A61B 5/0037
11,257,259 B2 * 2/2022 Teixeira .............. A61B 5/0033
11,257,586 B2 * 2/2022 Karanam .............. G06V 20/64
11,315,246 B2 * 4/2022 Innanje ............... A61B 5/0044
11,341,631 B2 * 5/2022 Song ................ G06F 18/24133
11,341,734 B2 * 5/2022 Han .................... A61B 5/1073
11,348,230 B2 * 5/2022 Sun ....................... G06N 20/00
11,354,833 B2 * 6/2022 Huang .............. G01R 33/5608
11,386,557 B2 * 7/2022 Hibbard ................. A61B 6/032
11,430,564 B2 * 8/2022 Karanam ............ G06V 10/764
11,445,994 B2 * 9/2022 Mansi .................. A61B 5/0077
11,461,929 B2 * 10/2022 Wu .......................... G06T 7/97
11,478,212 B2 * 10/2022 Singh .................... A61B 6/545
11,488,021 B2 * 11/2022 Sun ......................... G06N 3/09
11,494,877 B2 * 11/2022 Zhang ................... G06N 3/045
11,514,573 B2 * 11/2022 Huang .................. A61B 5/0044
11,538,159 B2 * 12/2022 Kluckner .............. H04N 23/90
11,557,391 B2 * 1/2023 Wu .................... G06F 18/2193
11,559,221 B2 * 1/2023 Tamersoy ........... A61B 5/0064
11,580,381 B2 * 2/2023 Daval Frerot .......... G06N 3/08
11,581,087 B2 * 2/2023 Rusko .................. G06T 7/0012
11,605,159 B1 * 3/2023 Do ...................... G06N 3/0464
11,605,216 B1 * 3/2023 Do ........................ G06V 10/60
11,610,307 B2 * 3/2023 Yip ........................ G06F 18/21
11,613,783 B2 * 3/2023 Rand ................... C12Q 1/6804
435/6.11
11,615,535 B2 * 3/2023 Huo ...................... G16H 10/60
382/131
11,663,727 B2 * 5/2023 Chen ................... A61B 5/0035
382/131
11,675,345 B2 * 6/2023 Bebak ............. G05B 19/41875
700/109
11,676,305 B2 * 6/2023 Wu .......................... G06T 7/97
702/85
11,682,098 B2 * 6/2023 Yip .......................... G06T 1/20
382/133
11,694,086 B2 * 7/2023 Gao ................... G06F 18/2413
382/103
11,703,373 B2 * 7/2023 Sa ........................ G01G 9/005
600/408
11,710,244 B2 * 7/2023 Sun ..................... A61B 5/1076
382/131
11,741,365 B2 * 8/2023 Khan .................... G06N 20/10
706/25
11,756,240 B2 * 9/2023 Innanje ................... G06T 1/20
382/131
11,769,254 B2 * 9/2023 Song ....................... G06N 3/02
382/128
11,774,535 B2 * 10/2023 Lyu ................... G01R 33/5608
324/309
11,776,171 B2 * 10/2023 Huang ................ G01R 33/543
11,786,129 B2 * 10/2023 Karanam .......... G06V 10/7796
11,803,939 B2 * 10/2023 Liu ....................... G06N 3/045
11,823,800 B2 * 11/2023 Wujek .................. G06N 3/045
11,836,925 B2 * 12/2023 Han .................... G06N 3/0464
11,836,946 B2 * 12/2023 Wu .......................... A61B 6/04
11,842,485 B2 * 12/2023 Tan ...................... G06T 7/0012
11,854,232 B2 * 12/2023 Wu .......................... G06T 7/74
11,933,870 B2 * 3/2024 Arroyo Camejo ..........................
G01R 33/5602
11,935,152 B2 * 3/2024 Yip .......................... G06T 1/20
11,935,230 B2 * 3/2024 Hölzer ................. G06T 7/0012
11,937,019 B2 * 3/2024 Barnehama ........... H04N 23/60
11,937,967 B2 * 3/2024 Wu .......................... G06N 3/02
11,941,732 B2 * 3/2024 Chen ..................... A61B 5/055
11,941,738 B2 * 3/2024 Karanam .............. G16H 50/20
11,948,250 B2 * 4/2024 Karanam ............ A61B 90/361
11,948,288 B2 * 4/2024 Chen ................. G01R 33/5608
11,963,741 B2 * 4/2024 Wu ...................... A61B 5/0035
11,967,004 B2 * 4/2024 Chen ..................... A61B 5/055
11,967,136 B2 * 4/2024 Sun ................... G06V 10/7747
12,014,815 B2 * 6/2024 Planche .............. H04N 13/243
12,026,122 B2 * 7/2024 Chen .................... G06F 16/116
12,026,913 B2 * 7/2024 Wu .......................... G06T 7/85
12,033,327 B2 * 7/2024 Cheng ...................... G06T 7/11
12,050,454 B2 * 7/2024 Bebak ................... G06V 10/82
12,051,186 B2 * 7/2024 Barnehama ........... G06V 10/82
12,051,204 B2 * 7/2024 Wu ....................... G06N 3/045
12,125,200 B2 * 10/2024 Chandolia ............ G06T 7/0012
12,136,220 B2 * 11/2024 Vasilev ............... G06N 3/0464
12,136,235 B2 * 11/2024 Zheng ................... G06N 3/084
12,138,015 B2 * 11/2024 Wu ...................... A61B 5/0035
12,165,236 B2 * 12/2024 Yip .......................... G06T 1/20
12,171,610 B2 * 12/2024 Zhang ................. A61B 5/0035
12,183,019 B2 * 12/2024 Karanam ................. G06T 7/75
12,186,913 B2 * 1/2025 Wu ........................ A61B 6/102
12,203,139 B2 * 1/2025 Rand ................... C12Q 1/6804
12,232,900 B2 * 2/2025 Zheng ................... A61B 6/469
12,277,712 B2 * 4/2025 Haslam .................. G06T 17/20
12,282,856 B2 * 4/2025 Zhang ................ G06F 18/2413
12,283,046 B2 * 4/2025 Min .................... A61B 6/5205
12,288,603 B2 * 4/2025 May ...................... G16H 20/10
12,299,885 B2 * 5/2025 Min ....................... A61B 5/055
12,324,695 B2 * 6/2025 Min .................... A61B 5/0066
12,324,696 B2 * 6/2025 Min .................... A61B 6/5217
12,340,569 B2 * 6/2025 Yoo ..................... G06N 3/0464
12,361,542 B2 * 7/2025 Braman ................ G06N 3/045

(56) References Cited

U.S. PATENT DOCUMENTS 12,380,560 B2 * 8/2025 Min ........................ A61B 6/027
12,387,329 B2 * 8/2025 Rix ........................ G06T 7/0012
12,396,695 B2 * 8/2025 Min ........................ A61B 5/0066
12,406,365 B2 * 9/2025 Min ........................ A61B 5/02007
12,437,187 B2 * 10/2025 Chen ........................ G06N 3/047
12,437,401 B2 * 10/2025 Planche ........................ G06T 7/0012
12,440,180 B2 * 10/2025 Min ........................ G06V 10/22
12,444,171 B2 * 10/2025 Zheng ........................ G06V 20/64
12,450,755 B2 * 10/2025 Planche ........................ G06T 7/246
12,450,793 B2 * 10/2025 Chen ........................ G06T 12/00
12,475,564 B2 * 11/2025 Ianni ........................ G06T 7/0012
12,482,108 B2 * 11/2025 Liu ........................ G06T 7/11
12,482,149 B2 * 11/2025 Sun ........................ G06T 12/10
2003/0215936 A1 * 11/2003 Kallioniemi ........................ G01N 1/36
435/40.5
2006/0064248 A1 * 3/2006 Saidi ........................ G06V 20/695
382/128
2007/0216909 A1 * 9/2007 Everett ........................ G01B 9/02089
356/479
2010/0111396 A1 * 5/2010 Boucheron ........................ G06F 18/29
382/133
2010/0158332 A1 * 6/2010 Rico ........................ A61B 5/0033
382/128
2014/0073922 A1 * 3/2014 Mammone ........................ A61B 8/13
600/440
2014/0086465 A1 * 3/2014 Wu ........................ G06T 7/11
382/131
2014/0140607 A1 * 5/2014 Erjefalt ........................ G06V 20/695
382/133
2014/0337052 A1 * 11/2014 Pellini ........................ G16H 70/60
705/3
2015/0100246 A1 * 4/2015 Remzi ........................ G16H 50/30
702/19
2015/0178938 A1 * 6/2015 Gorman, III ........................ G06T 7/174
382/131
2015/0302575 A1 * 10/2015 Sun ........................ G01W 1/10
382/103
2016/0063724 A1 * 3/2016 Tunstall ........................ G06T 7/136
382/128
2016/0103973 A1 * 4/2016 Singal ........................ G06F 16/245
705/3
2016/0253466 A1 * 9/2016 Agaian ........................ G06N 5/043
382/128
2017/0018116 A1 * 1/2017 Sun ........................ A61B 6/032
2017/0076442 A1 * 3/2017 Schoenmeyer ........................ G06T 11/26
2017/0109881 A1 * 4/2017 Avendi ........................ G06T 3/02
2017/0116497 A1 * 4/2017 Georgescu ........................ A61B 5/0044
2017/0140236 A1 * 5/2017 Price ........................ G06N 3/045
2017/0161455 A1 * 6/2017 Grady ........................ G16H 10/60
2017/0337682 A1 * 11/2017 Liao ........................ G06T 7/30
2017/0343635 A1 * 11/2017 Salerno ........................ A61B 5/0013
2017/0372155 A1 * 12/2017 Odry ........................ G06F 18/28
2017/0372193 A1 * 12/2017 Mailhe ........................ G06N 3/02
2018/0005136 A1 * 1/2018 Gai ........................ G06F 21/55
2018/0061058 A1 * 3/2018 Xu ........................ G06F 18/2411
2018/0061059 A1 * 3/2018 Xu ........................ G06N 3/045
2018/0089373 A1 * 3/2018 Matsuguchi ........................ C12N 15/1072
2018/0121759 A1 * 5/2018 Gabrani ........................ G06N 3/045
2018/0129911 A1 * 5/2018 Madabhushi ........................ G06F 18/214
2018/0218503 A1 * 8/2018 Xu ........................ G06N 3/045
2018/0232878 A1 * 8/2018 Braun ........................ G06T 7/20
2018/0239949 A1 * 8/2018 Chander ........................ G01N 33/5011
2018/0242946 A1 * 8/2018 Grbic ........................ A61B 8/58
2018/0315193 A1 * 11/2018 Paschalakis ........................ A61B 3/0025
2018/0330496 A1 * 11/2018 Ma ........................ A61B 6/032
2018/0340870 A1 * 11/2018 Gustafson ........................ C12Q 1/6806
2019/0034591 A1 * 1/2019 Mossin ........................ G06N 3/044
2019/0043242 A1 * 2/2019 Risser ........................ G06T 11/10
2019/0050992 A1 * 2/2019 Xu ........................ G06N 3/045
2019/0066301 A1 * 2/2019 Kartmann ........................ G06T 7/11
2019/0087532 A1 * 3/2019 Madabhushi ........................ G06F 18/2132
2019/0142358 A1 * 5/2019 Chen ........................ A61B 5/0035
600/427
2019/0295709 A1 * 9/2019 Chabin ........................ G06N 20/00
2019/0380656 A1 * 12/2019 Park ........................ A61B 5/055
2019/0392580 A1 * 12/2019 Kapil ........................ G06V 10/764
2020/0005497 A1 * 1/2020 Arberet ........................ G01R 33/4828
2020/0042873 A1 * 2/2020 Daval Frerot ........................ G06N 3/08
2020/0049785 A1 * 2/2020 Liu ........................ A61B 5/0037
2020/0051239 A1 * 2/2020 Braun ........................ G06T 7/0012
2020/0051257 A1 * 2/2020 Sauer ........................ G06T 7/344
2020/0057778 A1 * 2/2020 Sun ........................ G06N 3/0464
2020/0105417 A1 * 4/2020 Dolan ........................ G16H 50/30
2020/0167586 A1 * 5/2020 Gao ........................ G06N 3/084
2020/0400769 A1 * 12/2020 Arroyo Camejo ........................ G01R 33/5602
2020/0402237 A1 * 12/2020 Song ........................ G16H 50/20
2021/0121244 A1 * 4/2021 Innanje ........................ A61B 34/10
2021/0125707 A1 * 4/2021 Rusko ........................ G06T 7/11
2021/0158961 A1 * 5/2021 Sharma ........................ G16H 30/40
2021/0233251 A1 * 7/2021 Rothrock ........................ G06V 20/695
2021/0358629 A1 * 11/2021 Wujek ........................ G06N 3/045
2021/0383174 A1 * 12/2021 Hölzer ........................ G16H 30/20
2022/0012891 A1 * 1/2022 Nikolov ........................ A61B 5/7267
2022/0020145 A1 * 1/2022 Meister ........................ G06F 18/22
2022/0028085 A1 * 1/2022 Vasilev ........................ G06N 3/08
2022/0067935 A1 * 3/2022 Song ........................ G06N 3/02
2022/0083804 A1 * 3/2022 Gao ........................ G06F 18/2413
2022/0284570 A1 * 9/2022 Tan ........................ G06T 7/0012
2022/0284687 A1 * 9/2022 Han ........................ G06T 7/0012
2022/0351838 A1 * 11/2022 Pedemonte ........................ A61B 6/462
2023/0014745 A1 * 1/2023 Chen ........................ A61B 5/055
2023/0016765 A1 * 1/2023 Wu ........................ G06T 7/001
2023/0022030 A1 * 1/2023 Kanan ........................ G06V 10/82
2023/0109899 A1 * 4/2023 Zhang ........................ G06N 3/045
382/157
2023/0132479 A1 * 5/2023 Karanam ........................ G06T 13/40
345/419
2023/0132936 A1 * 5/2023 Wu ........................ A61B 6/54
378/62
2023/0135995 A1 * 5/2023 Chen ........................ A61B 5/055
382/131
2023/0140003 A1 * 5/2023 Karanam ........................ G06T 17/20
345/419
2023/0141392 A1 * 5/2023 Wu ........................ A61B 5/0035
345/419
2023/0169657 A1 * 6/2023 Wu ........................ G06N 3/045
382/128
2023/0169659 A1 * 6/2023 Chen ........................ G06T 3/18
382/131
2023/0196617 A1 * 6/2023 Zheng ........................ G06V 10/811
382/159
2023/0196742 A1 * 6/2023 Sun ........................ G06T 7/0012
382/128
2023/0326043 A1 * 10/2023 Sun ........................ G06T 7/246
2023/0346249 A1 * 11/2023 Laviolette ........................ A61B 5/055
2024/0055126 A1 * 2/2024 Wujek ........................ G06N 3/082
2024/0062857 A1 * 2/2024 Planche ........................ G16H 50/70
2024/0193772 A1 * 6/2024 Anderson ........................ G06T 7/0014
2024/0215945 A1 * 7/2024 Bunn ........................ G06T 7/0016
2025/0061581 A1 * 2/2025 Vasilev ........................ G16H 30/40
2025/0166791 A1 * 5/2025 Yu ........................ G06V 10/40
2025/0259433 A1 * 8/2025 Schmid ........................ G06V 10/82
2025/0266139 A1 * 8/2025 Zhao ........................ G16H 30/40
2025/0299802 A1 * 9/2025 Kunz ........................ G06N 3/0464

* cited by examiner

SYSTEMS AND METHODS FOR RECONSTRUCTING A 3D MEDICAL REPRESENTATION BASED ON SCREEN CAPTURES

BACKGROUND

During clinical visits or through online portals provided by a medical facility, patients are often presented with medical images such as two-dimensional (2D) or three-dimensional (3D) medical scans of the patients' anatomies via a display (e.g., a computer screen). While the patients may view the medical images on the display, they may not have means to access those images directly, much less the ability to analyze the images and obtain alerts, indications, or diagnoses about an abnormality in those anatomies if the images were accessible to the patients.

SUMMARY

Disclosed herein are systems, methods, and instrumentalities associated with reconstructing a 3D representation of an anatomical structure (e.g., a human organ) based on multiple screenshots that may be obtained via a screen recording. According to embodiments of the present disclosure, an apparatus may be configured to obtain multiple screenshots of a display (e.g., comprised in a video recording of the display) that may be captured while one or more medical representations (e.g., one or more medical scan images) of the anatomical structure are shown on the display. The apparatus may be further configured to extract a plurality of medical images of the anatomical structure from the multiple screenshots and determine one or more parameters for reconstructing a three-dimensional (3D) representation of the anatomical structure based on the plurality of extracted medical images. The apparatus may then reconstruct the 3D representation of the anatomical structure using the extracted medical images and the one or more determined parameters.

In examples, the multiple screenshots may be captured off the display of a desktop computer, a laptop computer, a tablet computer, or a mobile phone. In examples, the apparatus may receive the multiple screenshots from the tablet computer or the mobile phone. In examples, the apparatus may be the tablet computer or the mobile phone itself.

In examples, the apparatus may be further configured to detect, based on one or more pre-trained machine learning (ML) models and the 3D representation of the anatomical structure, an abnormality associated with the anatomical structure and provide an indication of the abnormality on the 3D representation of the anatomical structure. In examples, the apparatus may be further configured to generate, based on one or more pre-trained ML models and the 3D representation of the anatomical structure, a diagnostic report associated with the anatomical structure.

In examples, the one or more determined parameters may include a distance between two of the extracted medical images and/or a voxel size of the 3D representation. In examples, the apparatus may predict the distance between the two extracted medical images using a pre-trained ML model and determine the voxel size of the 3D representation based on the distance. In examples, the apparatus being configured to reconstruct the 3D representation of the anatomical structure based on the extracted medical images may comprise the apparatus being configured to identify one or more duplicates in the extracted medical images and exclude the one or more duplicates from the reconstruction of the 3D representation. In examples, the apparatus being configured to reconstruct the 3D representation of the anatomical structure based on the extracted medical images may comprise the apparatus being configured to adjust a size, an orientation, or an aspect ratio of at least one of the extracted medical images.

BRIEF DESCRIPTION OF THE DRAWINGS

A more detailed understanding of the examples disclosed herein may be obtained from the following descriptions, given by way of example in conjunction with the accompanying drawings.

DETAILED DESCRIPTION

The present disclosure is illustrated by way of example, and not by way of limitation, in the accompanying drawings. A detailed description of illustrative embodiments will be provided with reference to these drawings. Although the embodiments may be described with certain details, it should be noted that the details are not intended to limit the scope of the disclosure.

Figure 1:
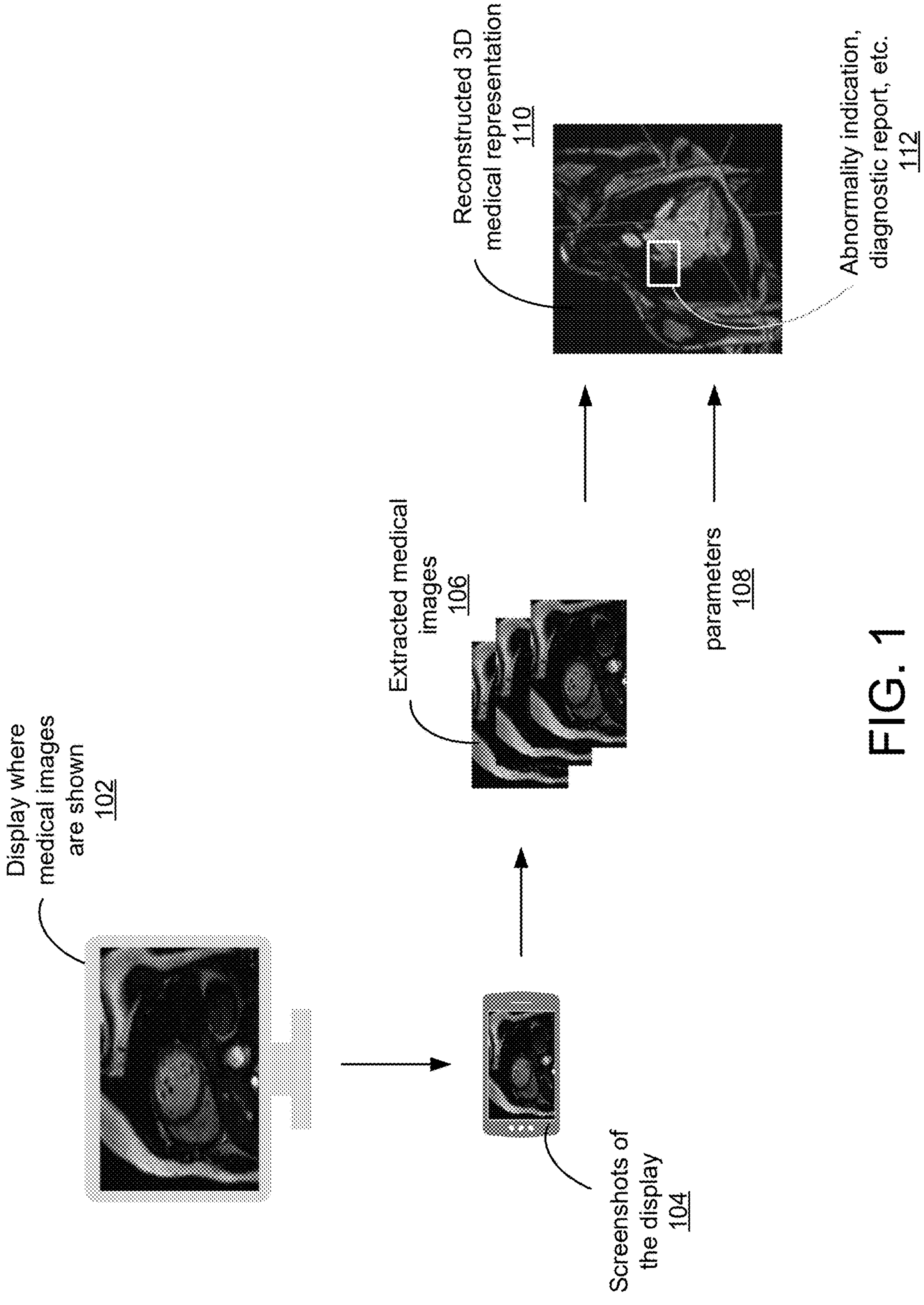
FIG. 1 is a simplified block diagram illustrating an example of reconstructing a 3D representation of an anatomical structure based on multiple screenshots of a display.

FIG. 1 illustrates an example of reconstructing a 3D representation of an anatomical structure (e.g., a human heart) based on multiple screenshots of a display. As shown in FIG. 1, the display (e.g., 102 of FIG. 1) may be a monitor or a screen such as the monitor of a desktop computer or a laptop computer, or the screen of a tablet computer or a mobile phone. The multiple screenshots 104 may be taken while a medical representation (e.g., a 2D or 3D computed tomography (CT) scan, magnetic resonance imaging (MRI) scan, or ultrasound scan) of the anatomical structure is shown on the display. For example, the multiple screenshots 104 may be part of a screen recording (e.g., a video) of a computer taken by a patient using a mobile device (e.g., a smart phone or tablet) during the patient's visit to a doctor's office, while medical scan images (e.g., CT, MRI, etc.) of the anatomical structure are shown to the patient using the computer. As another example, the multiple screenshots 104 may be recorded using a computer while a person is browsing medical scan images of the anatomical structure on the computer (e.g., via a patient portal accessible through a web browser installed on the computer). While the examples provided in this disclosure may treat the multiple screenshots 104 as part of a video recording, those skilled in the art will appreciate that the multiple screenshots 104 may also be taken individually, for example, as photos instead of the video recording.

According to embodiments of the present disclosure, the multiple screenshots 104 may be processed to extract a plurality of medical images 106 (e.g., which may also be referred to herein as slices) of the anatomical structure based on the multiple screenshots. The processing may be performed by a computing apparatus including, for example, a mobile device or a server. For instance, the processing may be performed by a mobile device (e.g., a tablet computer or a mobile phone) that was used to capture the multiple screenshots 104. The processing may also be performed by a server device (e.g., on a computing cloud) that may receive the multiple screenshots 104 from a mobile device used to capture the screenshots. The processing may also be performed by the computer on which the multiple screenshots 104 are recorded. As will be described in greater detail below, the processing may include identifying duplicated medical images from the multiple screenshots 104 and excluding those duplicate medical images from the plurality of medical images 106. The processing may also include adjusting the size, orientation, and/or aspect ratio of at least a subset of the plurality of medical images 106 (e.g., so that the plurality of medical images may be aligned for subsequent processing).

Since the plurality of medical images 106 is extracted from the multiple screenshots 104 of the display 102, the plurality of medical images 106 may correspond to those shown on the display 102 while the multiple screenshots 104 are taken. Once obtained, the plurality of medical images 106 may be used, together with one or more determined parameters 108, to reconstruct a 3D representation 110 of the anatomical structure. The one or more parameters 108 may include, for example, a slice thickness, a pixel spacing, physical dimensions covered by a slice, a voxel size of the 3D representation, a distance between two (e.g., any two) of the extracted medical images 106, and/or the like. As will be described in greater detail below, the one or more parameters 108 may be determined in different ways including, for example, extracting the parameters from the multiple screenshots 104 (e.g., via optical character recognition (OCR)) or predicting the parameters using one or more pre-trained machine-learning (ML) models.

The 3D representation of the anatomical structure 110 reconstructed based on the extracted medical images 106 and the one or more determined parameters 108 may correspond to the representation (e.g., 2D or 3D medical scan) shown on the display 102, and may be used for diagnostic purposes, treatment planning, and/or surgical navigation. For example, the 3D representation 110 may be used to detect an abnormality associated with the anatomical structure and provide an indication 112 (e.g., a bounding box, a segmentation mask, etc.) of the abnormality (e.g., on the 3D representation 110). As another example, the 3D representation 110 may be used to generate a diagnostic report associated with the anatomical structure based on features extracted from the 3D representation. As yet another example, the 3D representation 110 may be used to generate a treatment plan associated with the anatomical structure based on the extracted features of the 3D representation and/or a medical history of the concerned patient. As will be described in greater detail below, one or more of these tasks may be accomplished using pre-trained ML models.

Figure 2:
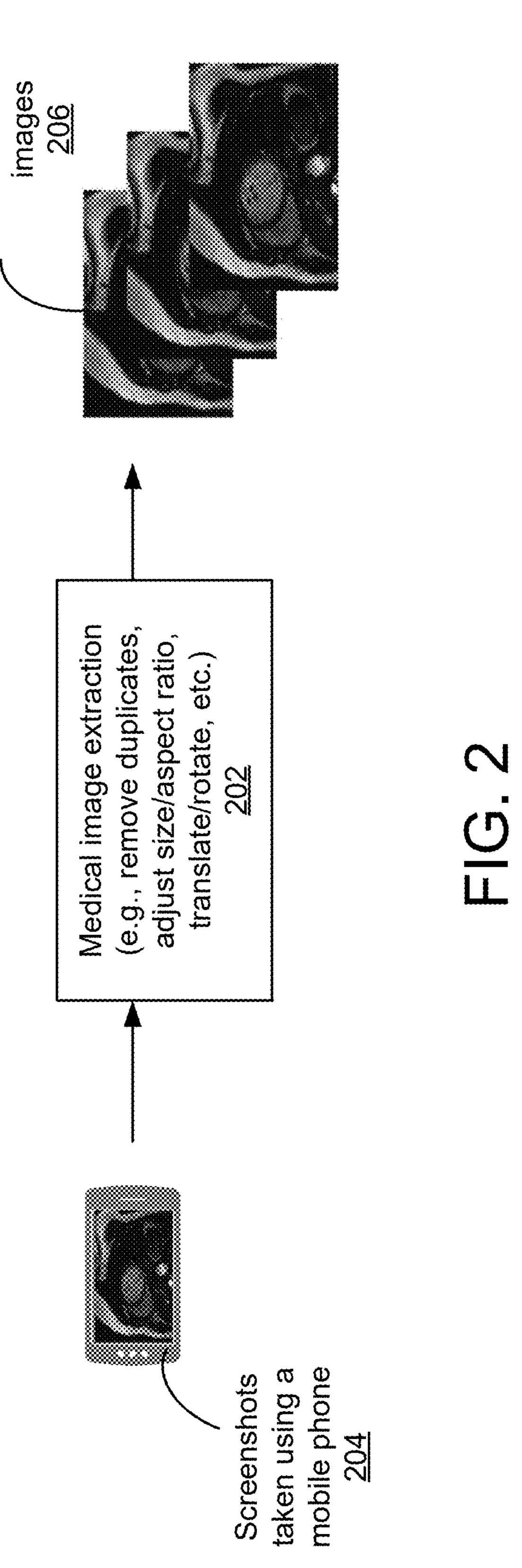
FIG. 2 is a simplified block diagram illustrating an example of extracting medical images from multiple screen shots.

FIG. 2 illustrates an example of extracting medical images from a plurality of screen shots. As explained above, the screenshots (e.g., 204 of FIG. 2) may be captured using a mobile device while a medical representation (e.g., 2D or 3D medical scans) of an anatomical structure is shown on a display device. Due to the nature of such screen capturing, the screenshots 204 may not be directly suitable for reconstructing a 3D representation of the anatomical structure (e.g., the screenshots 204 may include duplicated images, images of different sizes or aspect ratios, images of poor quality, etc.). Therefore, the multiple screenshots 204 may be processed at 202 to extract a plurality of qualifying medical images 206 that may be used for the 3D reconstruction and, as part of the extraction process, one or more of the following may be performed.

The operations at 202 may include image preprocessing. For example, from a captured screenshot containing a medical image (e.g., a 2D medical image), four corners of the medical image may be determined (e.g., using a machine learning model trained for detecting visual features associated with the corners), and a bounding box may be derived based on the four corners and used to crop the medical image out from the screenshot. This way, only the medical image may be extracted from the screenshot while the remaining parts of the screenshot (e.g., such as unrelated GUI components showing on the screen) may be ignored. As another example, normalization may be applied to the medical images extracted from the screenshots 204 to ensure that they have consistent lighting and/or color correction to reduce discrepancies. As yet another example, resizing, upsampling, or downsampling may be performed to speed up processing while retaining sufficient detail. As yet another example, one or more filters (e.g., a Gaussian filter, a median filter, etc.) may be applied to reduce the noise in the images and to improve image quality.

The operations at 202 may include aligning the medical images extracted from the screenshots 204. The alignment may involve adjusting the geometric properties (e.g., size, aspect ratio, etc.) of the extracted medical images, and/or translating/rotating them to match corresponding points or features across multiple images to establish their relative positions and/or orientations. For example, distinct points of interest (e.g., keypoints) in each extracted image may be identified using feature detection algorithms such as SIFT (Scale-Invariant Feature Transform), SURF (Speeded-Up Robust Features), and/or ORB (Oriented FAST and Rotated BRIEF). For each detected keypoint, a descriptor may be computed to represent the feature (e.g., local appearance) around the keypoint (e.g., the descriptor may include a vector that represents the unique characteristics of the feature). The descriptors between images may then be matched to find corresponding points, and the closest matches may be determined based on one or more distance metrics (e.g., Euclidean distance).

In some examples, the matched keypoints may not all be correct due to noise, occlusion, repetitive textures, etc., so geometric verification may be performed to improve the alignment of the images. For example, an RANSAC (Random Sample Consensus) based filter matching technique may be used to estimate a robust transformation (e.g., a transformation matrix) that may align the images while discarding outliers. In some examples, if the extracted medical images are not already aligned on the same plane, rectification may be performed to bring corresponding points into alignment. This may be done, for example, where two screenshots are captured from slightly different viewpoints.

The operations at 202 may include detecting and excluding duplicated medical images (e.g., including medical images that are not exactly the same but are substantially similar) extracted from the screenshots 204. This may be accomplished by comparing the extracted medical images based on their visual content (e.g., rather than their file names or metadata). For example, the duplicated medical images may be identified using a hashing method with which a hash representing the visual content of an extracted medical image may be calculated and the duplicated medical images may be detected as having similar hashes. As another example, the duplicated medical images may be identified using a feature-based method with which key points and/or descriptors in an image may be identified and compared to find similar or duplicate images. As yet another example, the duplicated medical images may be identified using a deep learning-based approach that may utilize an artificial neural network such as, for example, a convolutional neural network (CNN). The neural network may be pre-trained to extract deep features from the medical images, and the features may then be compared using one or more similarity measures (e.g., cosine similarity, Euclidean distance, etc.) to detect duplicates in the medical images.

As shown in FIG. 1, certain parameter(s) 108 may be needed to reconstruct the 3D representation of the anatomical structure (e.g., based on the set of medical images 206 extracted from the multiple screenshots 204 shown in FIG. 2). The parameter(s) may include, for example, the number of medical images included in the extracted image set, a distance between consecutive images or slices in the extracted image set, the physical dimensions represented by a voxel in the 3D reconstruction, etc. In some examples, the parameter(s) may be obtained based on an external input (e.g., a user may provide the parameter(s)), while in other examples, the parameter(s) may be determined based on the set of medical images 206 or the screenshots 204 (e.g., by extracting information from the images or screenshots via OCR, or by predicting the parameter(s) using a pre-trained machine learning model).

Figure 3:
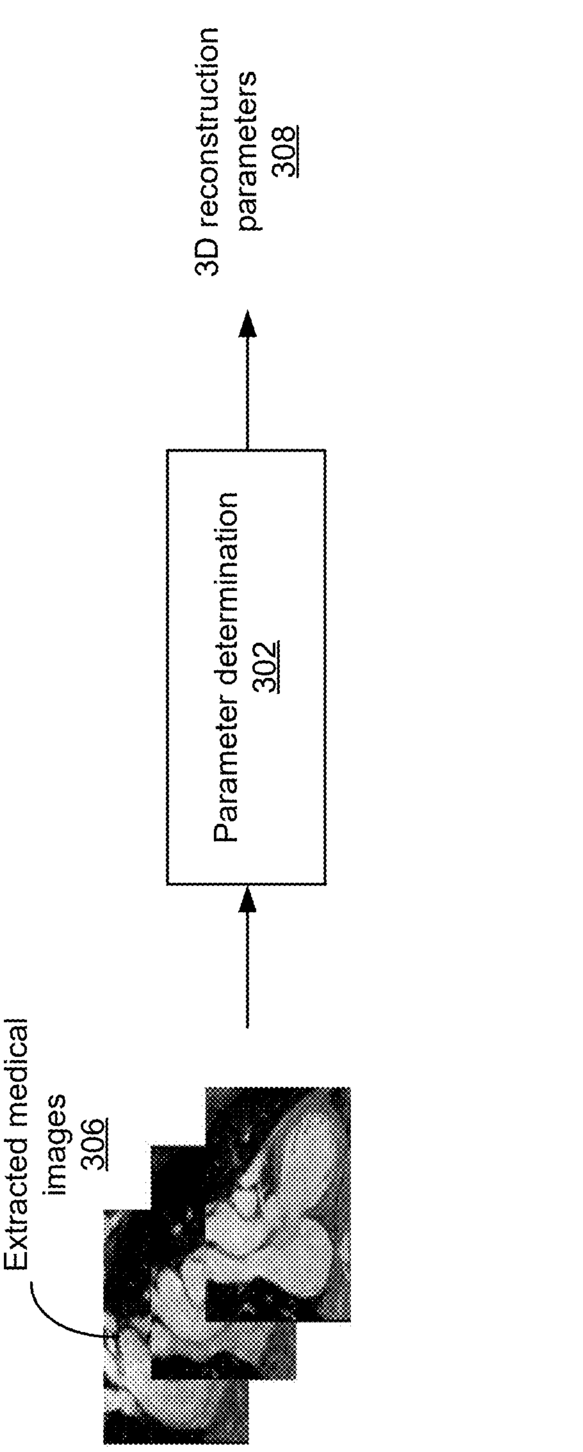
FIG. 3 is a simplified block diagram illustrating an example of determining one or more 3D reconstruction parameters based on medical images extracted from multiple screenshots.

FIG. 3 illustrates an example process for determining one or more 3D reconstruction parameters (e.g., 308 of FIG. 3) based on medical images (e.g., 306 of FIG. 3) extracted from a screen recording (e.g., comprising multiple screenshots). The parameter determination may be performed at 302 and may use various techniques including conventional or deep learning based techniques. Using the determination of a voxel size for the 3D reconstruction as an example, such a parameter may be estimated based on the images 306 (e.g., 2D images) such as the physical dimensions of the images, the image resolution (e.g., the number of pixels in the 2D image by width×height), and/or a slice thickness that may be represented by the distance between consecutive 2D images or slices. The estimation may involve, for example, determining the pixel size in physical units and further determining the voxel size in the in-plane dimensions (x, y) and the z-dimension (e.g., the z-dimension measure may be determined based on the slice thickness mentioned above).

In examples, the voxel size may be predicted using a pre-trained ML model such as a deep learning (DL) model. Such an ML model may be implemented using various neural network architectures including, for example, a CNN, a ResNet, etc. The ML model may be trained in through a training process that may involve providing a plurality of 2D medical images to the ML model, forcing the ML model to make a prediction about a voxel size, comparing the predicted voxel size to corresponding ground truth, and adjusting the parameters of the ML model based on a loss between the predicted voxel size and the ground truth.

While the parameter determination at 302 is described using the voxel size as an example, those skilled in the art will appreciate that similar techniques may be applied to derive other parameters (e.g., the distance between consecutive images or slices) that may be needed for the 3D reconstruction.

Using the one or more parameters estimated according to FIG. 3 and a series of medical images (e.g., CT or MRI images) extracted from a screen recording (e.g., as shown in FIGS. 2), 3D medical image reconstruction may be performed to create a 3D representation of an anatomical structure (e.g., a patient's anatomy), as shown by 110 of FIG. 1. One or more of the following operations may be performed as part of the 3D reconstruction process. Other operations described above (e.g., image resizing/normalization, image registration or alignment, image denoising, etc.) may also be performed as part of the 3D reconstruction process. For example, the 3D reconstruction process may include identifying a region of interest (ROI) in the series of input images. This may be accomplished using various segmentation techniques such as, e.g., thresholding, region growing, or deep learning methods, with which the boundaries of organs, tissues, or other structures within each input image may be delineated. A 3D grid (e.g., voxel grid) may then be created to represent the volume that encompasses the input images or slices. The grid may be defined, for example, based on the dimensions and voxel size estimated from the 2D images (e.g., as discussed earlier). The intensity values of voxels between consecutive 2D slices may then be estimated, for example, using one or more interpolation techniques such as linear or cubic splines. As a result of the interpolation, a continuous 3D volume may be created, which may be visualized using various volume rendering techniques like ray-casting, maximum intensity projection (MIP), or surface rendering.

In examples, the 3D reconstruction may also include one or more post-processing steps to enhance or improve the reconstructed 3D representation. For example, one or more smoothing filters may be applied to reduce any artifacts from the reconstruction and enhance important features such as the edges of the anatomical structure. In addition, anatomical knowledge or machine learning-based correction methods may be used to adjust for errors in the segmentation or interpolation.

The 3D image (e.g., 110 of FIG. 1) of the anatomical structure reconstructed using the techniques described herein may be analyzed for diagnostic purposes, treatment planning, and/or surgical navigation. The analysis may be performed using conventional methods such as by performing volumetric measurements, distance calculations, morphological studies, or edge detection on the reconstructed 3D data. The analysis may also be performed using machine learning (e.g., deep learning) based techniques such as by training machine learning models to detect abnormalities in the anatomical structure and generate indications, reports, or treatment plans associated with the detected abnormalities (e.g., as shown by 112 of FIG. 1).

The machine learning (ML) model(s) used for the abnormality detection and/or report generation may include a CNN-based ML model, a transformer-based ML model, a large language model (LLM), and/or other types of deep learning models. The ML model(s) may be trained on actual patient medical images (e.g., 2D or 3D medical scans) to learn and extract features from those medical images, and recognize the features that may be associated with an abnormality. As will be described in greater detail below, the ML model(s) may be trained based on large volumes of clinical data and, more specifically, by splitting the data into training, validation, and test sets, training the model on the training set and validating it on the validation set (e.g. using appropriate loss functions, like binary cross-entropy, dice loss, etc.).

In examples, the abnormality detection and/or report generation may be accomplished using the reconstructed 3D representation in conjunction with other types of information (e.g., the data used to train the ML model(s) and generate the diagnoses may be multi-modal). These other types of information may include, for example, textual information such as a description of the symptoms experienced by a patient, lab reports of the patient, medical histories of the patient, etc. The information may also include other medical images of the patient such as, for example, MRI or CT images of the patient. The information may further include audio information such as the recording of a conversation between the patient and a physician, the patient's own narrated description of their health conditions, etc.

The ML models(s) may be trained using the multi-modal patient data and once trained, deployed to generate an output (e.g., 112 of FIG. 1) based on the multimodal patient data including the reconstructed 3D representation. One or more of the ML models may be implemented using an artificial neural network that may include multiple encoders and a decoder. Each of the encoders may be configured to receive a respective type of patient data and generate an encoded representation of the type of patient data (e.g., in the form of one or more vectors). The decoder may be configured to receive the encoded representations of the multimodal patient data (e.g., a concatenation of the encoded representations) and predict the output based on the encoded representations and/or an inquiry (e.g., a question posted by a patient). As described herein, the predicted output may include a medical decision such as a medical procedure (e.g., an MRI or CT scan) recommend for the patient, an indication of whether tumorous areas have been detected in the 3D representation, etc. The predicted output may also include a medical summary (e.g., a textual summary) of the health conditions of the patient generated based on the encoded representations.

In examples, one or more of the encoders may include a CNN comprising one or more convolutional layers, one or more pooling layers, and/or one or more fully connected layers. Each of the convolutional layers may include multiple kernels or filters with respective weights that may be configured to extract features from an input (e.g., a textual input or an image-based input). The convolution operations may be followed by batch normalization and/or an activation function (e.g., such as a rectified linear unit (ReLu) activation function), and the features extracted by the convolutional layers may be downsampled via the one or more pooling layers and/or fully connected layers to obtain a representation of the extracted features, for example, in the form of a feature vector. In examples, the network may employ a recurrent architecture to store hidden states associated with the input and feed the hidden states back into the convolutional layers (e.g., via one or more recurrent connections) of the encoder. This way, the encoder may, during feature encoding, utilize not only the current set of data samples passing through the network, but also previous data samples represented by the hidden states to derive a more accurate representation of the input data.

In examples, one or more of the encoders may include a transformer neural network with a built-in attention (e.g., self-attention) mechanism (e.g., comprising one or more self-attention layers) configured to detect the relationship between different parts of an input data sequence and learn the context (and thus the meaning) of the input data. These tasks may be accomplished, for example, based on query, key and value vectors or matrices.

In examples, the ML models described herein may include a vision-language model that may be trained to learn a mapping between visual and textual embeddings (e.g., between visual and textual features) from a dataset comprising paired images and textual descriptions. The training data may be obtained from various sources including, for example, the Internet (e.g., websites that may include images and descriptions of the content of the images), publicly accessible databases (e.g., figures and captions from repositories of academic publications), hospital records (e.g., radiology reports), etc. The training data may be pre-processed, for example, to ensure that it is in a suitable format for the training. The pre-processing may, for example, include resizing the images, tokenizing the text, creating pairs of image-text inputs, etc. The pre-processing may also include augmenting the training data (e.g., by varying the textual descriptions to increase the diversity of the training dataset) to improve the robustness and accuracy of the vision-language model.

The vision-language model may include a vision encoding portion (e.g., implemented via a vision encoder) and a text encoding portion (e.g., implemented via a text encoder). In examples, the vision encoder may utilize a vision transformer architecture designed to extract image features from input images, while the text encoder may be implemented using a regular transformer architecture designed to extract text features from textual descriptions. The image features and text features may then be aligned (e.g., mapped to each other) in a joint embedding space (e.g., through concatenation or some other suitable fusion techniques) to capture the relationships between the visual and textual information. In examples, the vision encoder and the text encoder may be trained first (e.g., separately) on a large number of images and textual descriptions, respectively, and then fine-tuned using an application specific dataset (e.g., a certain type of medical scan images) and/or based on a specific downstream task (e.g., medical image classification).

The training may allow the vision-language model to acquire an understanding of the relationships between certain visual and textual embeddings or features such that, when given an image (e.g., the 3D representation 110 of FIG. 1) as an input, the vision-language model may extract visual features from the input and generate a coherent and informative explanation (e.g., a diagnostic report) of the visual information contained in the input by relating the extracted visual features to corresponding textual features in the learned joint embedding space.

Figure 4:
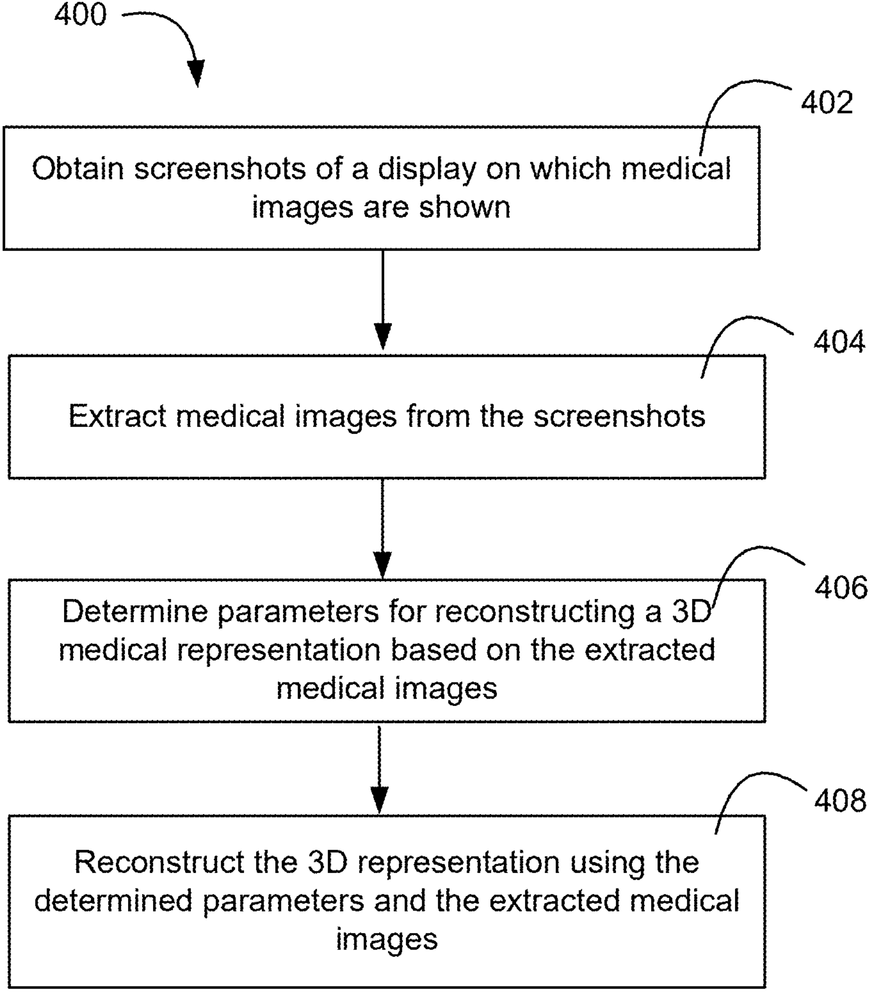
FIG. 4 is a flow diagram illustrating example operations associated with reconstructing a 3D representation of an anatomical structure based on a set of screenshots.

FIG. 4 illustrates an example procedure 400 that may include one or more of the operations described herein. The procedure 400 may be performed by various devices, independently or collaboratively. For example, the procedure 400 may be performed by a server (e.g., in a computing cloud) configured to receive screen recordings of a display from another device (e.g., a mobile device). The procedure 400 may also be performed by the device (e.g., a mobile device or a desktop computer) used to capture the screenshots.

As shown in FIG. 4, the procedure 400 may include obtaining, at 402, multiple screenshots of a display, wherein the multiple screenshots may be captured while a medical representation of an anatomical structure is shown on the display. The procedure 400 may further include extracting a plurality of medical images (e.g., 2D medical images) of the anatomical structure from the multiple screenshots at 404, and determining, at 406, one or more parameters for reconstructing a 3D representation of the anatomical structure using the plurality of extracted medical images. The procedure 400 may additionally include reconstructing the 3D representation of the anatomical structure at 408 based on the plurality of medical images extracted from the screenshots and the one or more determined parameters.

Figure 5:
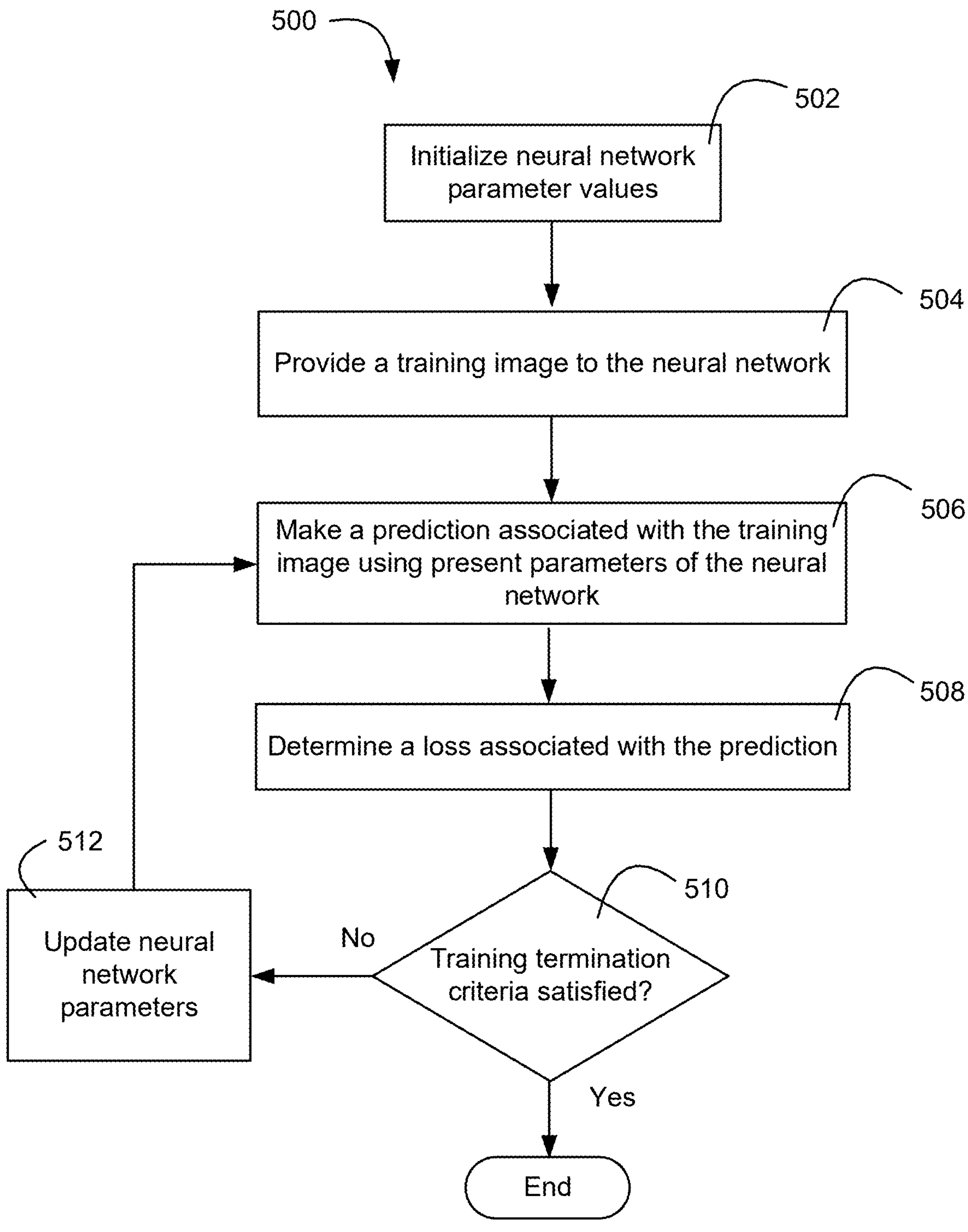
FIG. 5 is a flow diagram illustrating example operations associated with training an artificial neural network to perform one or more of the tasks described in embodiments of the present disclosure.

FIG. 5 illustrates example operations 500 that may be associated with training an artificial neural network (e.g., which may be configured to implement one or more of the ML models described herein) to perform one or more of the tasks described herein. As shown in FIG. 5, the training operations 500 may include initializing the operating parameters of the neural network (e.g., weights associated with various layers of the neural network) at 502, for example, by sampling from a probability distribution or by copying the parameters of another neural network having a similar structure. The training operations may further include providing an input (e.g., a reconstructed 3D medical image) to the neural network at 504 and causing the neural network to make a prediction (e.g., about a classification label, a segmentation mask, etc.) using presently assigned network parameters at 506. At 508, the training operations may include determining a loss associated with the prediction, for example, based on a difference between the prediction and corresponding ground truth. At 510, the training operations may further include determining whether one or more training termination criteria have been satisfied. For example, the training termination criteria may be determined to have been satisfied if the difference between the prediction and the ground truth falls below a predetermined threshold value. If the determination at 510 is that the training termination criteria are satisfied, the training may end. Otherwise, the presently assigned network parameters may be adjusted at 512, for example, by backpropagating a gradient descent of the loss through the network, before the training returns to 506.

For simplicity of explanation, the training operations are depicted and described herein with a specific order. It should be appreciated, however, that the training operations may occur in various orders, concurrently, and/or with other operations not presented or described herein. Furthermore, it should be noted that not all operations that may be included in the training process are depicted and described herein, and not all illustrated operations are required to be performed.

Figure 6:
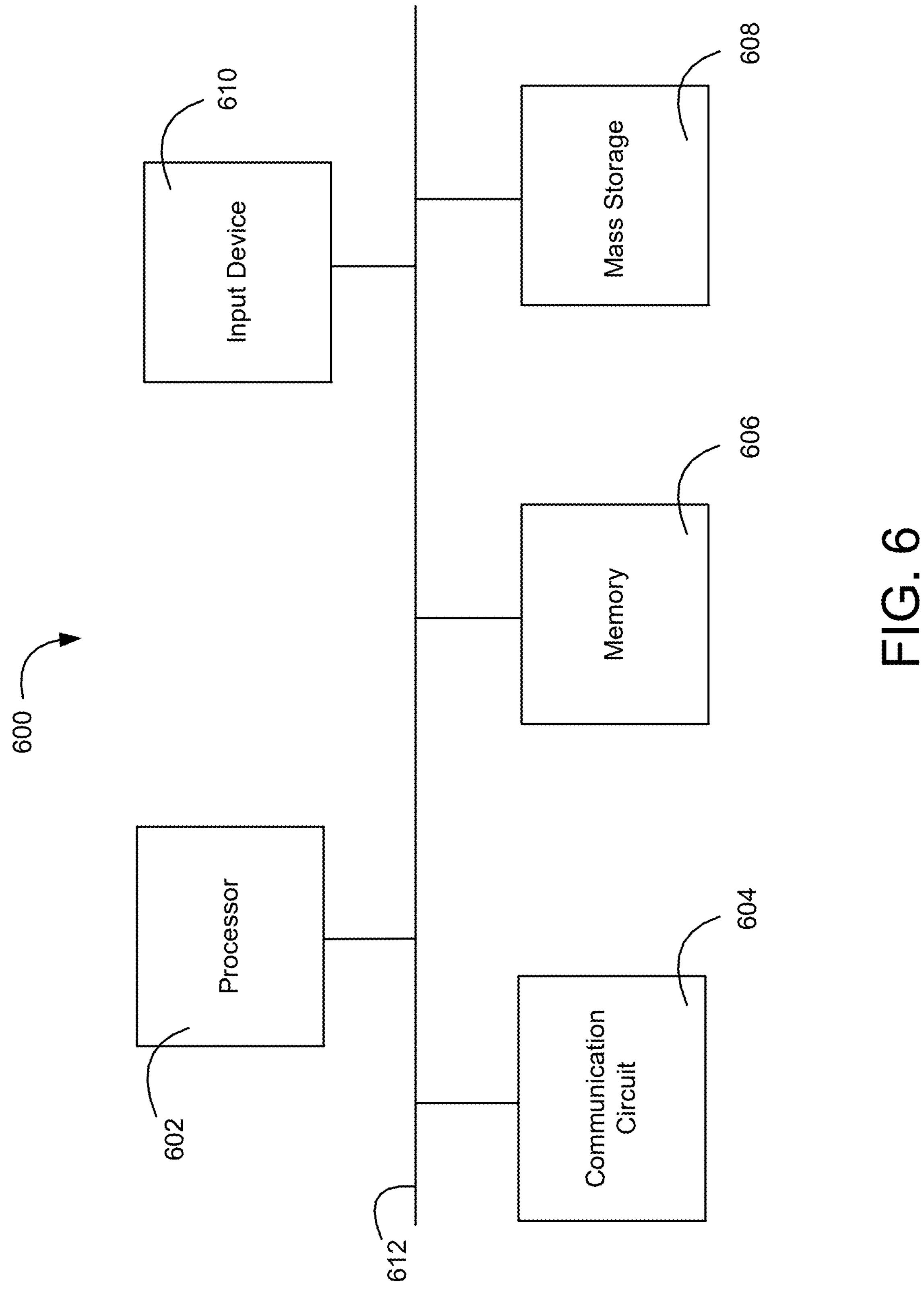
FIG. 6 is a simplified block diagram illustrating an example apparatus that may be configured to perform one or more of the tasks described in embodiments of the present disclosure.

The systems, methods, and/or instrumentalities described herein may be implemented using one or more processors, one or more storage devices, and/or other suitable accessory devices such as display devices, communication devices, input/output devices, etc. FIG. 6 is a block diagram illustrating an example apparatus 600 that may be configured to perform the tasks described herein. As shown, apparatus 600 may include a processor (e.g., one or more processors) 602, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. Apparatus 600 may further include a communication circuit 604, a memory 606, a mass storage device 608, an input device 610, and/or a communication link 612 (e.g., a communication bus) over which the one or more components shown in the figure may exchange information.

The communication circuit 604 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 606 may include a storage medium (e.g., a non-transitory storage medium) configured to store machine-readable instructions that, when executed, cause the processor 602 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 608 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 602. The input device 610 may include a keyboard, a mouse, a voice-controlled input device, a touch sensitive input device (e.g., a touch screen), and/or the like for receiving user inputs to apparatus 600.

It should be noted that apparatus 600 may operate as a standalone device or may be connected (e.g., networked, or clustered) with other computation devices to perform the functions described herein. And even though only one instance of each component is shown in FIG. 6, a skilled person in the art will understand that apparatus 600 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

The term "computer-readable storage medium" used herein may include any tangible medium that is capable of storing or encoding a set of instructions for execution by a computer that cause the computer to perform any one or more of the methods described herein. The term "computer-readable storage medium" used herein may include, but not be limited to, solid-state memories, optical media, and magnetic media.

The invention claimed is:

1. An apparatus, comprising:

one or more processors configured to:

obtain multiple screenshots of a display, wherein the multiple screenshots were captured by a mobile phone or a tablet while a medical representation of an anatomical structure is shown on the display;

extract a plurality of medical images of the anatomical structure from the multiple screenshots, wherein, as part of the extraction, the one or more processors are configured to:

crop, from the multiple screenshots, respective areas that correspond to the medical representation of the anatomical structure, wherein the cropping is performed based at least on visual features extracted from the multiple screenshots; and process the cropped areas to derive the plurality of medical images, wherein, during the processing, a size, an orientation, or an aspect ratio of at least one of the cropped areas is adjusted and at least one duplicate in the cropped areas is detected and eliminated;

determine one or more parameters for reconstructing a three-dimensional (3D) representation of the anatomical structure based on the plurality of extracted medical images, wherein the one or more parameters include a distance between two of the plurality of extracted medical images and a voxel size for the 3D representation, the distance predicted using a pre-trained machine learning (ML) model, the voxel size determined based on the distance; and reconstruct the 3D representation of the anatomical structure based on the plurality of extracted medical images and the one or more determined parameters.

2. The apparatus of claim 1, wherein the multiple screenshots were captured off the display of a desktop computer, a laptop computer, the tablet, or the mobile phone.

3. The apparatus of claim 2, wherein the multiple screenshots were captured off the display of the tablet or the mobile phone, and wherein the one or more processors are configured to receive the multiple screenshots from the tablet or the mobile phone.

4. The apparatus of claim 3, wherein the apparatus is the tablet or the mobile phone.

5. The apparatus of claim 1, wherein the multiple screenshots were captured as a screen recording of the display.

6. The apparatus of claim 1, wherein the one or more processors are further configured to detect, based on one or more pre-trained machine learning (ML) models and the 3D representation of the anatomical structure, an abnormality associated with the anatomical structure and provide an indication of the abnormality on the 3D representation of the anatomical structure.

7. The apparatus of claim 1, wherein the one or more processors are further configured to generate, based on one or more pre-trained machine learning (ML) models and the 3D representation of the anatomical structure, a diagnostic report associated with the anatomical structure.

8. A method for reconstructing a three-dimensional (3D) representation of an anatomical structure, the method comprising:

obtaining multiple screenshots of a display, wherein the multiple screenshots were captured by a mobile phone or a tablet while a medical representation of the anatomical structure is shown on the display;

extracting a plurality of medical images of the anatomical structure from the multiple screenshots, wherein the extraction comprises:

cropping, from the multiple screenshots, respective areas that correspond to the medical representation of the anatomical structure, wherein the cropping is performed based at least on visual features extracted from the multiple screenshots; and processing the cropped areas to derive the plurality of medical images, wherein, during the processing, a size, an orientation, or an aspect ratio of at least one of the cropped areas is adjusted and at least one duplicate in the cropped areas is detected and eliminated;

determining one or more parameters for reconstructing the 3D representation of the anatomical structure based on the plurality of extracted medical images, wherein the one or more parameters include a distance between two of the plurality of extracted medical images and a voxel size for the 3D representation, the distance predicted using a pre-trained machine learning (ML) model, the voxel size determined based on the distance; and reconstructing the 3D representation of the anatomical structure based on the plurality of extracted medical images and the one or more determined parameters.

9. The method of claim 8, wherein the multiple screenshots were captured off the display of a desktop computer, a laptop computer, the tablet, or the mobile phone.

10. The method of claim 8, wherein the multiple screenshots were captured as a screen recording of the display.

11. The method of claim 8, further comprising detecting, based on one or more pre-trained machine learning (ML) models and the 3D representation of the anatomical structure, an abnormality associated with the anatomical structure and providing an indication of the abnormality on the 3D representation of the anatomical structure.

12. The method of claim 8, further comprising generating, based on one or more pre-trained machine learning (ML) models and the 3D representation of the anatomical structure, a diagnostic report associated with the anatomical structure.

13. A non-transitory storage medium comprising instructions that, when executed by a processor included in a computing device, cause the processor to implement the method of claim 8.

* * * * *